United States Patent [19]

Moon et al.

[11] 4,235,933
[45] Nov. 25, 1980

[54] PROCESS FOR CONVERTING WHEY PERMEATE TO OIL-CONTAINING YEAST

[75] Inventors: Nancy J. Moon, Griffin, Ga.; Earl G. Hammond, Ames, Iowa

[73] Assignee: Iowa State University Research Foundation, Inc., Ames, Iowa

[21] Appl. No.: 902,242

[22] Filed: May 2, 1978

[51] Int. Cl.³ .......................... A23C 9/12; A23L 1/28; C12N 1/16; C12R 1/72

[52] U.S. Cl. ...................................... 426/41; 426/60; 435/255; 435/921

[58] Field of Search ............... 426/41, 60, 62; 195/82; 435/255, 921

[56] References Cited

U.S. PATENT DOCUMENTS

| | | | |
|---|---|---|---|
| 3,818,109 | 6/1974 | Bechtle | 426/41 |
| 3,968,257 | 7/1976 | Müller | 195/82 X |

OTHER PUBLICATIONS

Zalashko, et al., Growth of Yeasts on Various Types of Whey, Chemical Abstracts, vol. 81:48511s, 1974 (p. 305).

Webb, et al., By Products From Milk, 2nd Ed. The Avi Publ. Co., Inc., Westport, Conn., 1970 (pp. 47-52).

Moon, et al., Conversion of Cheese Whey to Yeast Oil and Protein, J. Amer. Oil Chemists Soc., vol. 54, No. 2, Feb. 1977, (p. 156A).

Kaneko et al., Lipid Composition of 30 Species of Yeasts Lipids vol. 11, 1976 (pp. 837-844).

Errin, J. A., Comparative Biochemistry of Fatty Acids in Eukaryotic Microorganisms. Academic Press, Inc., N. Y. 1973, (pp. 114-117).

*Primary Examiner*—David M. Naff
*Attorney, Agent, or Firm*—Tilton, Fallon, Lungmus & Chestnut

[57] ABSTRACT

The solids of whey permeate obtained by ultrafiltration are converted to a triglyceride oil-containing yeast cell mass by fermentation with fat-producing strains of *Candida curvata*. For maximum oil yield, the fermentation is continued until at least 90% of the lactose has been consumed, such as 98 to 99% of the lactose. The resulting oil-containing yeast cell mass can be further processed to prepare animal feed materials, and/or for recovery of the oil by extraction. The spent fermentation medium has relatively low COD indicating that the fermentation not only removes the lactose but also most of the other organic material.

5 Claims, No Drawings

PROCESS FOR CONVERTING WHEY PERMEATE TO OIL-CONTAINING YEAST

BACKGROUND AND PRIOR ART

We have previously proposed that whey might be fermented with yeasts which are capable of producing substantial amounts of fatty acids triglycerides (fat or oil). Moon, N. J. & Hammond, E. G., Abst. 202, J. Amer. Oil Chemists Soc., Feb., 1977, Vol. 54, No. 2, p. 156 A. Further, the lipid composition of a wide variety of yeasts has been studied and reported. Kaneko, et al, "Lipid Composition of 30 Species of Yeasts," *Lipids* 11: 837–844 (1976). Species of the genus Candida were referred to but not *Candida curvata*. See also Erwin, J. A., "Comparative Biochemistry of Fatty Acids in Eukaryotic Microorganisms," in *Lipid and Biomembranes of Eukaryotic Microorganisms*, J. A. Erwin, Ed., Academic Press, N. Y., pp. 114–117 (1973).

U.S. Pat. No. 3,818,109 of Robert M. Bechtle describes the conversion of whey solids to an edible yeast cell mass. A combination of bacteria and yeasts are employed for the fermentation, and it is indicated that the yeasts may include species of the genera Candida. *Candida curvata* is not mentioned, and there is no suggestion that the yeast cell mass would contain oil. In the Bechtle process, the medium is prepared from concentrated whey containing whey protein and lactose in the same proportions as in the usual whey obtained from cheese manufacturing operations.

Liquid whey resulting from cheese manufacturing operations is processed by ultrafiltration to prepare a whey protein concentrate. A by-product of such ultrafiltration is referred to as "whey permeate". It consists of the liquid and dissolved solids which pass through the ultrafiltration membranes. The permeate solids can be recovered, such as by condensation of the permeate liquid in an evaporator, and further treatment in a spray dryer to produce the permeate solids as a dry powdery material. Such permeate solids, however, have limited uses and their commercial value is relatively low compared to the whey protein concentrate which may contain 30% or more protein. The permeate solids are composed principally of lactose together with a minor amount of nitrogenous material (polypeptides, amino acids, etc.). Since whey protein concentrate is prepared on a large scale in the United States with the resulting whey permeate by-product, there has been a recognized need to find new uses for the permeate material, and/or to develop processes for modifying and improving the value of the permeate material.

SUMMARY OF INVENTION

In connection with research on the conversion of whey to yeast lipid and single cell protein, we have discovered that fat-producing strains of *Candida curvata* are capable of efficiently converting whey lactose to a triglyceride oil-containing yeast cell mass. It was further discovered that whey permeate is a better media for promoting lipid formation by *Candida curvata* than unmodified whey. Apparently the protein of natural whey is not utilized to any appreciable extent, and substantially less triglyceride oil is formed from the same amount of available lactose. The soluble protein material of whey permeate appears to be more available for use by the yeast cells, and the fermentation can be conducted so as to consume most of the lactose with resulting increased yield of lipid.

In our process, the fermentation is preferably continued beyond the growth phase of the cells into a fattening phase where the production of visible droplets of oil in the cells can be detected. In general, the fermentation is desirably continued until at least 90% of the lactose has been consumed, such as 98 to 99%. Most of the other organic material is also consumed by the fermentation. The fermentation is conducted under conditions which favor the growth of the yeast cells including aeration.

The process of the present invention thereby provides a means for converting whey permeate into a product of increased value. The conversion of the lactose to a triglyceride oil retains most of the energy of the carbohydrate. Further, if desired, the oil can be harvested from the cells by organic solvent extraction. The residual cell mass can be incorporated into animal feeds or used as a source of single cell protein. Alternatively, the oil-containing yeast cell mass can be processed with oil extraction to prepare an animal feed material of high energy content. The spent fermentation medium can be readily disposed of because of its low COD.

DETAILED DESCRIPTION

The starting material for the process of the present invention is readily available commercially in the form of whey permeate solids, a dry powdery material which is readily soluble in water. If the present process is operated in conjunction with a cheese plant, the whey permeate can be utilized in liquid form either with or without additional condensation. As used herein and in the art generally, the term "whey permeate solids" is understood as referring to the solids obtained as a by-product of ultrafiltration of whey. Suitable equipment for manufacturing whey protein concentrate with a whey permeate by-product is manufactured and sold by Romicon, Inc., of Woborn, Maryland, and other manufacturers. Hollow fiber membranes are employed for producing the ultrafiltrate, such as the "XM 50" membranes supplied by Romicon. The membranes vary with respect to molecular weight cut-off, but are generally in the range of 20,000 to 60,000 dalton. For example, the "XM 50" membrane has a molecular weight cut-off of approximately 50,000. In other words, the ultrafiltrate (whey protein concentrate) contains the whey protein material having a molecular weight in excess of 50,000 dalton, while the lower molecular protein material passes through the membranes and is found in the permeate. Lactose and inorganic metal salts also pass through the membrane and are present in the permeate liquid. The permeate may then be condensed in an evaporator and spray dried to produce a whey permeate product in solid form. A typical analysis of such a product is lactose-80%, protein-4%, ash-10%, water-balance.

As a first step in the process, an aqueous fermentation medium is prepared from the permeate solids. The content of the permeate solids in the medium may range from 2 to 25% by weight, but a medium is preferably utilized containing about 4 to 12% by weight of permeate solids. As indicated above, such media can be prepared directly from liquid whey permeate. The solids concentration of the liquid permeate can be adjusted by evaporation of water or addition of permeate solids, as required. The medium need not be completely sterile, and may contain harmless lactic acid producing bacteria. As is well known in the art, the bacterial count of the media can be easily controlled by pasteurization and/or hydrogen peroxide treatment.

The whey permeate medium can be used as such, or additives may be incorporated to promote the growth of the yeast cells. One of the advantages of the process of the present invention is that the whey permeate is in itself an almost ideal medium for the production of triglyceride oil-containing *Candida curvata* yeast cells. However, the growth of the yeast cells may be promoted by adding a small amount of a nitrogen source, such as ammonium hydroxide or ammonium sulfate. Other additives such as yeast extract or metal salts provide relatively slight growth stimulation. The amount of nitrogen which can be advantageously added as ammonium hydroxide or ammonium sulfate can range from about 9 to 10 millimoles of nitrogen per liter of liquid.

The prepared medium is then inoculated with the *Candida curvata* culture. In general, an actively-growing inoculum can be prepared in permeate or other suitable medium. The volume of such inoculum can be about 9 to 90% of the volume of the medium for rapid fermentation. Higher inoculum levels than this could be prepared by centrifugation of an actively-growing culture.

More specifically, stock cultures of the yeast can be maintained on a sample medium such as malt extract agar. Cultures can be revived by transfer to fresh media, incubated at 32 C for 1 week and then stored under refrigeration. Before a fermentation, a part of an actively growing culture from a malt extract slant is inoculated into a small volume of whey permeate. Then this is aerated by shaking on a platform rotary shaker at about 32 C for 2 days. It is used as an inoculum for a larger volume of whey permeate usually at an addition ratio of inoculum to permeate of 1:10. This process is continued until an inoculation for a fermentation is reached at 1:10 (or a 10% inoculation by volume). Alternatively, the inoculum can come from part of the preceding batch or from cell paste recovered from centrifugation of actively growing cultures. If this is done about 2 g wet cell paste per liter would be comparable to a 10% inoculum.

The yeast to be used in the process should be a strain of the *curvata* species of the genus Candida. While it appears that all strains of *Candida curvata* naturally produce some lipid on fermentation of lactose, not all strains of *Candida curvata* can be considered as "fat-producing" under the conditions of the process, that is, producing visible droplets of fat in a substantial proportion of the yeast cells. Two particularly suitable strains of *Candida curvata* which produce high yields of triglyceride oil under the conditions of the process have been deposited with the American Type Culture Collection, Rockville, Maryland. One of these is *Candida curvata* strain D, ATCC No. 20509, and the other is *Candida curvata* strain R, ATCC No. 20508. While both of these strains produce oil in high yield, the best conversion of lactose to oil is obtained with strain D. Other available strains of *Candida curvata* can be utilized, but appear to be less desirable. However, the suitability of any particular strain of *Candida curvata* for use in the process can be readily determined by culturing the strain on whey agar (6.5% dried whey and 1.5% agar). After growth for seven days, the culture can be examined microscopically for fat production. If at least 5 to 10% of the cells contain visible fat droplets, the strain may be considered as fat-producing, and can be expected to convert a whey permeate media to a triglyceride oil-containing yeast cell mass. Under microscopic examination, intracellular fat droplets can be readily observed of a size of at least 1.2 microns or larger.

After the whey permeate medium has been inoculated with the fat-producing strain of *Candida curvata*, it is subjected to aerated fermentation according to known procedures. The pH of the medium should be adjusted within a range favoring the growth of the yeast cells, and fermentation should be carried out at a favorable temperature for growth of the yeast cells. In general, pH's of from about 5.0 to 6.2 can be used, and usually the optimum pH will be in the range from about 5.2 to 5.8. For pH adjustments, standard reagents such as hydrochloric acid or sodium hydroxide can be used, and pH adjusting agents can be added during the fermentation to maintain the pH at the desired level. In general, fermentation temperatures in the range from 27 to 37 C can be used. The most favorable temperature appears to be from about 27 to 31 C. These conditions, however, are not unique for the process of this invention, but rather are typical conditions for culturing yeast organisms.

It is also conventional to utilize aeration to promote the growth of yeast cells in submerged culture fermentation. See, for example, Bechtle U.S. Pat. No. 3,818,109. It will be understood that optimum aeration may vary with the particular strain of *Candida curvata* as well as with the stage of the fermentation. In general, the amount of aeration may range from about 0.2 to 0.8 liters of air per minute per liter of medium. It has been found advantageous to utilize aeration levels in the lower portion of this range for the initial part of the fermentation (the growth phase) and an aeration level in the upper portion of this range for the latter part of the fermentation (the fattening phase). For example, an aeration level of 0.2 to 0.3 liters air/min/liter medium can be utilized for the growth phase of the yeast, and an aeration level of 0.6 to 0.8 liters air/min/liter medium during the fattening phase.

In the culturing of microorganisms, the stage referred to as the growth phase is well known. It is characterized by a sharp increase in cell count and is, therefore, usually referred to as the logarithmic growth phase. For the purpose of the present invention, it is desirable to continue the fermentation past the growth phase and into a second phase which may be referred to as the fattening phase. In the latter phase, the cell count remains relatively constant, but the total cell mass increases. The triglyceride oil appears to be formed mainly in the latter stage of the fermentation after most of the lactose in the medium has been consumed. In general, the fermentation should be continued until the yeasts have utilized at least 90% of the lactose of the medium. Most of the other organic material will also be consumed. For example, on completion of the fermentation, the medium may contain only from 1 to 2% of the starting lactose, and on a COD basis the medium may contain as little as 5 to 10% of the total starting organic material. Preferably the fermentation is continued until at least 85% of the total organic material has been consumed as measured by the reduction in chemical oxygen demand (COD) of the medium. The fermentation can usually be completed in about 60 to 80 hours. Good results are obtained with fermentation times of about 72 hours. If desired, the progress of the fermentation can be followed by withdrawing samples of the fermentation broth periodically and examining the yeast cells. As the fermentation nears completion, the content of fat droplets in the yeast cells will be readily observable by microscopic examination. On a dry weight basis, the yeast cell mass on completion of the fermentation may contain over 40% by weight of triglyceride oil, such as 47 to 56%.

The oil produced by the process of the present invention comprises primarily a mixture of triglycerides of oleic and palmitic acids. The oil also contains lesser amounts of stearic acid and linoleic acid triglycerides. An illustrative composition on a fatty acid basis is: 50% oleic, 30% palmitic, 15% stearic, and 6% linoleic.

The triglyceride oil containing cell mass can be separated from the fermentation broth by centrifutation and further processed to prepare a dry feed material. For example, the cell mass can be drum-dried. To make the yeast cells more readily digestible by non-ruminant domestic animals, the walls of the yeast cells can be disrupted by homogenization or sonication prior to drying. The resulting dried product can be utilized as a feed for domestic animals, such as cattle and swine.

If desired, the yeast cell mass after removal of the fermentation broth can be extracted with an organic solvent to recover the oil. To promote oil liberation, the cells can be disrupted, such as by homogenization or sonication. The cells may also be digested with an acid to promote liberation of the oil, such as digestion with 2N HCl at 70° C. for 5 hours. The organic solvents which can be advantageously used for the extraction include methanol, benzene, and mixtures of methanol and benzene. A sequential extraction with a series of organic solvents can be used to maximize the oil recovery, such as extraction with methanol, followed by methanol-benzene (1:1 v/v), and finally by a benzene extraction. Other useable solvents include ethanol and hexane. A mixture of ethanol and hexane is particularly desirable.

After the extraction of the oil, it can readily be recovered by evaporation of the volatile organic solvent, such as by distillation of the solvent under reduced pressure. The resulting oil either with or without further purification can be utilized as a food material, since it will be essentially pure fatty acid triglycerides similar in general composition to known animal fats or vegetable oils.

The process of this invention is further illustrated by the following experimental examples.

EXAMPLES

Whey permeate was prepared from Swiss whey with a Dorr-Oliver ultrafilter equipped with a polysulfone membrane with a 24,000 dalton rejection limit. The permeate was concentrated and frozen until used. The fermentations were carried out in a 14-liter fermenter equipped with air flow, temperature, and agitation controls. The basic medium was the whey permeate reconstituted to 5.5% solids and sterilized prior to use. For the tests with Candida curvata strain R, the following additives were used: 0.320 mg/l NH4OH, 2.5 mg/l MnSO4, and 5.3 mg/l K2HOP4. For Candida curvata strain D only ammonium hydroxide was added in the amount of 0.097 mg/l. At the start of the fermentation, the medium was saturated with air and 10% by volume inoculum was added. The inoculum was an actively-growing culture of the yeast in permeate that had been aerated by shaking at room temperature for about 24 hrs.

The conditions for the fermentations are summarized below in Table A.

TABLE A

| Conditions | Growth Phase | | Fattening Phase | |
|---|---|---|---|---|
| | Strain R | Strain D | Strain R | Strain D |
| pH | 5.8 | 5.4 | 5.2 | 5.8 |
| temp. (°C.) | 30 | 28 | 30 | 28 |
| air flow* | 0.25 | 0.25 | 0.7 | 0.7 |

*liters air/min./liter medium

The completion of the growth phase and the start of the fattening phase was determined by a gradual decline in cell division and consequently a relatively constant cell number. At this stage larger fat droplets began to appear in cells signaling the onset of the fattening phase.

All fermentations were continued for 72 hours. Periodically 200-ml samples were withdrawn from the fermenter, and a portion was centrifuged in a refrigerated centrifuge. The recovered cells were washed once in distilled water, recentrifuged and frozen until analyzed. The results are summarized below in Table B.

TABLE B

Fermentation of Whey Permeate with *Candida curvata*

| C. curvata | Strain R | Strain D |
|---|---|---|
| Fermentation time (hr) | 72 | 72 |
| Generation time (hr) | 1.63 | 1.10 |
| Generations/hr | 0.61 | 0.91 |
| Maximum cell no. $\times 10^8$/ml | 8.7 | 5.2 |
| Rate fat[a] produced | .280 | .288 |
| Rate lactose[b] used | 2.8 | 3.3 |
| Cell mass[a] production | .470 | .404 |
| Lactose[c] start | 65.0 | 57.4 |
| Lactose[c] used | 63.9 | 56.8 |
| Soluble protein[c,d] start | 2.91 | 2.22 |
| Soluble protein[c,d] end | .625 | 1.99 |
| COD mg/liter start | 73,000 | 63,000 |
| COD mg/liter end | 7,000 | 3,000 |
| COD% reduction | 90 | 95 |
| Final cell yield[c] | 25.7 | 26.8 |
| Oil produced[c] | 13.0 | 15.6 |
| Cell protein[c] | 2.25 | 2.47 |
| Oil coefficient[e] | 20 | 27 |
| % Oil dry wt | 51 | 57 |
| % Protein dry wt | 9 | 9 |

[a]Maximum rate (g/hr/liter) was usually at 40 hr.
[b]Maximum rate (mM/hr/liter) during the fattening period.
[c]Grams/liter medium.
[d]This includes the nitrogen added as NH4OH and calculated as protein (%N $\times$ 6.25 = % protein).
[e]Oil coefficient = (g oil produced/g lactose used) $\times$ 100.
[f]COD = chemical oxygen demand.

The analyses reported in the above table were carried out as follows:

A Max Levy mold-counting chamber was used for direct microscopic counts on medium diluted usually 1:10, with water. Cells with buds and pseudomycelium were counted as two cells when the daughter cell was ½ the size of the mother cell. For dry weight 2-to 10-ml samples of fermentation liquor were filtered through a tared 0.45-μmembrane filter (Millipore Corporation, Bedford, Mass.), the filter was washed with 5 ml water, dried under vacuum 12 h at 45 C and weighed. A blank made with uninoculated fermentation media was subtracted. Nitrogen was determined by the Kjeldahl method. COD was determined on centrifuged medium by chromate oxidation. American Public Health Association, Inc. 1967, Standard methods for the examination of water and waste water, 12th Ed. American Public Health Association, I Uc., New York, N.Y. Glucose, galactose and lactose in spent fermentation medium were determined by the enzymatic method of Hettinga et al. J. Diary Sci. 53: 1377-1380 (1970). Only glucose determinations were made on most samples, because this proved the more reliable procedure, and there was little free galactose. Nitrogen was determined by the Kjeldahl method.

The fatty acid composition of the oil produced by the fermentation of the whey permeate was determined by analysis. The results are summarized in Table C.

TABLE C

Fatty Acid Compositions of Oil Produced By Fermentation of Whey Permeate with C. curvata

| Yeast Used | Fatty Acids (%) | | | |
|---|---|---|---|---|
| | Palmitic | Stearic | Oleic | Linoleic |
| C. curvata strain R Tr[a] | 31 | 12 | 51 | 6 |
| C. curvata strain D Tr | 32 | 15 | 44 | 8 |

[a]Tr = Detected but less than 1%.

The analyses reported in the above table were conducted as follows:

Fatty acids were extracted with hexane from an alcoholic KOH digest of wet cells. The fatty acids were converted to methyl esters according to Luddy et al. Luddy, F. E., R. A. Barford, S. E. Herb, and P. Magedman, 1968, A rapid and quantitative procedure for the preparation of methyl esters of butter oil and other fats, J. Am. Oil Chemists Soc. 45: 549-552. The methyl esters were analyzed by gas liquid chromatography on a Beckman GC-5 chromatograph equipped with a flame ionization detector and a 180×0.3-cm stainless steel column was packed with 15% EGS5X on 100/120 mesh Chromosorb P (Applied Science Lab. Inc., State Park, PA.). Oven temperature was 185 C, and the carrier was gas helium at 50 ml/min. Peak areas were integrated by an Autolab 1600 (Spectro Physics, Mountain View, CA.). A standard ester mixture was used to calibrate the instrument.

ANIMAL FEED MATERIALS

Animal feed materials can be prepared from the triglyceride oil-containing yeast cells. In one procedure, the triglyceride oil-containing cell mass is harvested from the spent fermentation medium by centrifugation. The cell mass can be dried by spray drying or drum-drying, and fed in dried form to ruminant animals. The dried cells may be peletized or otherwise prepared in granular form. For non-ruminant animals, the digestibility of the feed material can be improved by subjecting the wet recovered cell mass to homogenization, for example, one or more times at 10,000 PSI to break the yeast cell walls. See Cunningham et al J. Food Science 40: 732-735 (1975). The homogenized yeast can then be drum-dried to produce the non-ruminant feed material. Animal feed materials thus prepared will provide a very high energy ration.

For producing oil together with a lower energy feed material, the wet cell mass after centrifugation is subjected to solvent extraction. The extracting solvents may be used in sequence. For example, the cell mass may be first extracted with methanol, followed by a methanol-benzene mixture (1:1) and finally by benzene. Alternatively, the sequential extraction may utilize hexane, hexane-ethanol (1:1), and ethanol. Each of the solvents may be used in a volume approximately ten times the weight of the cell mass, and may be left in contact with the cells for 20 minutes. Oil recovered from the extracts can be refined for human consumption.

The solvents can be recovered from the cell mass, leaving an oil-free and solvent-free cell residue. This residue may contain about 20% protein, and either as such, or after drum-drying can be used as a feed material for ruminant or non-ruminant animals.

We claim:

1. A process for converting the solids of whey permeate to a triglyceride oil-containing yeast cell mass, said permeate solids having been obtained by ultrafiltration of whey and being composed principally of lactose together with a minor amount of soluble protein, comprising the steps of:
   (a) preparing an aqueous fermentation medium from said permeate solids, said medium containing from 2 to 25% by weight of said permeate solids;
   (b) inoculating said medium with a fat-producing strain of Candida curvata, said strain being capable of producing visible droplets of fat in the yeast cells of a size of at least 1.2 microns; and
   (c) subjecting said medium to aerated fermentation until at least 90% of the lactose therein has been consumed and the yeast cells have reached the fattening growth phase with visible droplets of fat therein of a size of at least 1.2 microns, said yeast cells on a dry weight basis on completion of said fermentation containing at least 40% by weight triglyceride oil.

2. A process for converting the solids of whey permeate to a triglyceride oil-containing yeast cell mass, said permeate solids having been obtained by ultrafiltration of whey and being composed principally of lactose together with a minor amount of soluble protein, comprising the steps of:
   (a) preparing an aqueous fermentation medium from said permeate solids, said medium containing from 2 to 25% by weight of said permeate solids;
   (b) inoculating said medium with Candida curvata strain R (ATCC No. 20508) yeast cells; and
   (c) subjecting said medium to aerated fermentation until at least 90% of the lactose therein has been consumed and the yeast cells have reached the fattening growth phase with visible droplets of fat therein of a size of at least 1.2 microns, said yeast cells on a dry weight basis on completion of said fermentation containing at least 40% by weight triglyceride oil.

3. A process for converting the solids of whey permeate to a triglyceride oil-containing yeast cell mass, said permeate solids having been obtained by ultrafiltration of whey and being composed principally of lactose together with a minor amount of soluble protein, comprising the steps of:
   (a) preparing an aqueous fermentation medium from said permeate solids, said medium containing from 2 to 25% by weight of said permeate solids;
   (b) inoculating said medium with Candida curvata strain D (ATCC No. 20509) yeast cells; and
   (c) subjecting said medium to aerated fermentation until at least 90% of the lactose therein has been consumed and the yeast cells have reached the fattening growth phase with visible droplets of fat therein of a size of at least 1.2 microns, said yeast cells on a dry weight basis on completion of said fermentation containing at least 40% by weight triglyceride oil.

4. The process of claim 1 in which said whey permeate is obtained from Swiss cheese whey using a membrane with a 24,000 dalton rejection limit.

5. The process of claim 4 in which said yeast is selected from the class consisting of Candida curvata strain R (ATCC No. 20508) and Candida curvata strain D (ATCC No. 20509).

* * * * *